(12) United States Patent
Tigno, Jr.

(10) Patent No.: US 9,283,095 B2
(45) Date of Patent: Mar. 15, 2016

(54) SYSTEMS AND METHODS FOR MAGNETIZED STENT HAVING GROWTH-PROMOTING PROPERTIES

(75) Inventor: Teodoro Aclan Tigno, Jr., Gaithersburg, MD (US)

(73) Assignee: The Henry M. Jackson Foundation for the Advancement of Military Medicine, Inc., Bethesda, MD (US)

( * ) Notice: Subject to any disclaimer, the term of this patent is extended or adjusted under 35 U.S.C. 154(b) by 143 days.

(21) Appl. No.: 13/805,295

(22) PCT Filed: Jul. 6, 2011

(86) PCT No.: PCT/US2011/043100
§ 371 (c)(1),
(2), (4) Date: Jan. 15, 2013

(87) PCT Pub. No.: WO2012/006373
PCT Pub. Date: Jan. 12, 2012

(65) Prior Publication Data
US 2013/0110225 A1    May 2, 2013

Related U.S. Application Data

(60) Provisional application No. 61/361,835, filed on Jul. 6, 2010.

(51) Int. Cl.
*A61F 2/82* (2013.01)
*A61F 2/856* (2013.01)

(52) U.S. Cl.
CPC . *A61F 2/82* (2013.01); *A61F 2/856* (2013.01); *A61F 2002/823* (2013.01); *A61F 2210/009* (2013.01); *A61F 2250/0031* (2013.01); *A61F 2250/0051* (2013.01)

(58) Field of Classification Search
CPC ....... A61F 2/0063; A61F 2/062; A61F 2/082; A61F 2/852; A61F 2/856; A61F 2250/0051; A61F 2002/823; A61L 27/3826; A61L 27/3839
USPC .......................................................... 600/12
See application file for complete search history.

(56) References Cited

U.S. PATENT DOCUMENTS

| | | | | |
|---|---|---|---|---|
| 5,059,166 A | * | 10/1991 | Fischell et al. | 600/3 |
| 5,817,126 A | * | 10/1998 | Imran | 623/1.15 |
| 5,951,599 A | * | 9/1999 | McCrory | 606/108 |
| 6,093,199 A | * | 7/2000 | Brown et al. | 606/200 |
| 6,315,709 B1 | * | 11/2001 | Garibaldi et al. | 600/12 |

(Continued)

*Primary Examiner* — Ryan J Severson
*Assistant Examiner* — Christian Knauss
(74) *Attorney, Agent, or Firm* — MH2 Technology Law Group, LLP

(57) ABSTRACT

Embodiments relate to systems and methods for magnetized stent having growth-promoting properties. A stent assembly comprising a tubular elongated body having a magnetized region and a tissue nidus area is inserted beneath the orifice of a vascular aneurysm. The magnetic region can serve to attract and position both residual red blood cells and magnetically nano-ireated growth-promoting cells to the orifice area of the aneurysm. The outer circumference of the tubular elongated body can act as a floor or scaffold for regenerated smooth vascular muscle cells. In embodiments, the tissue nidus area can be provided on the exterior stent, while the magnetized region is provided on the interior stent, of a stent-in-stent structure. In embodiments, the exterior stent is made of biodegradable material which gradually dissolves or dissipates in situ.

16 Claims, 3 Drawing Sheets

(56) References Cited

U.S. PATENT DOCUMENTS

| | | | |
|---|---|---|---|
| 6,663,607 B2* | 12/2003 | Slaikeu et al. | 604/265 |
| 7,156,871 B2* | 1/2007 | Jones et al. | 623/1.13 |
| 7,572,288 B2* | 8/2009 | Cox | 623/1.17 |
| 7,615,373 B2* | 11/2009 | Simpson et al. | 435/398 |
| 2002/0133219 A1* | 9/2002 | Barry | 623/1.15 |
| 2003/0018294 A1* | 1/2003 | Cox | 604/20 |
| 2003/0065355 A1* | 4/2003 | Weber | 606/200 |
| 2003/0139802 A1* | 7/2003 | Wulfman et al. | 623/1.15 |
| 2003/0199993 A1* | 10/2003 | Gellman et al. | 623/23.75 |
| 2004/0030379 A1* | 2/2004 | Hamm et al. | 623/1.15 |
| 2004/0186562 A1* | 9/2004 | Cox | 623/1.42 |
| 2005/0004653 A1* | 1/2005 | Gerberding et al. | 623/1.13 |
| 2005/0107870 A1* | 5/2005 | Wang et al. | 623/1.44 |
| 2005/0137680 A1* | 6/2005 | Ortiz et al. | 623/1.16 |
| 2005/0271697 A1* | 12/2005 | Litvack | 424/423 |
| 2006/0008472 A1* | 1/2006 | Huang et al. | 424/204.1 |
| 2006/0025713 A1* | 2/2006 | Rosengart et al. | 604/5.02 |
| 2006/0025848 A1* | 2/2006 | Weber et al. | 623/1.15 |
| 2006/0041182 A1* | 2/2006 | Forbes et al. | 600/12 |
| 2006/0193887 A1* | 8/2006 | Owens et al. | 424/423 |
| 2006/0286137 A1* | 12/2006 | Sandhu et al. | 424/422 |
| 2007/0168016 A1* | 7/2007 | Gronemeyer et al. | 623/1.16 |
| 2007/0190037 A1* | 8/2007 | Flugelman | 424/93.7 |
| 2008/0065200 A1* | 3/2008 | Binyamin et al. | 623/1.35 |
| 2008/0071353 A1* | 3/2008 | Weber et al. | 623/1.15 |
| 2008/0086201 A1* | 4/2008 | Weber et al. | 623/1.42 |
| 2008/0294232 A1* | 11/2008 | Viswanathan | 623/1.11 |
| 2009/0062900 A1* | 3/2009 | Lal et al. | 623/1.15 |
| 2009/0287297 A1* | 11/2009 | Cox | 623/1.22 |
| 2009/0295383 A1* | 12/2009 | Gianchandani et al. | 324/252 |
| 2009/0319020 A1* | 12/2009 | Kassab | 623/1.11 |

* cited by examiner

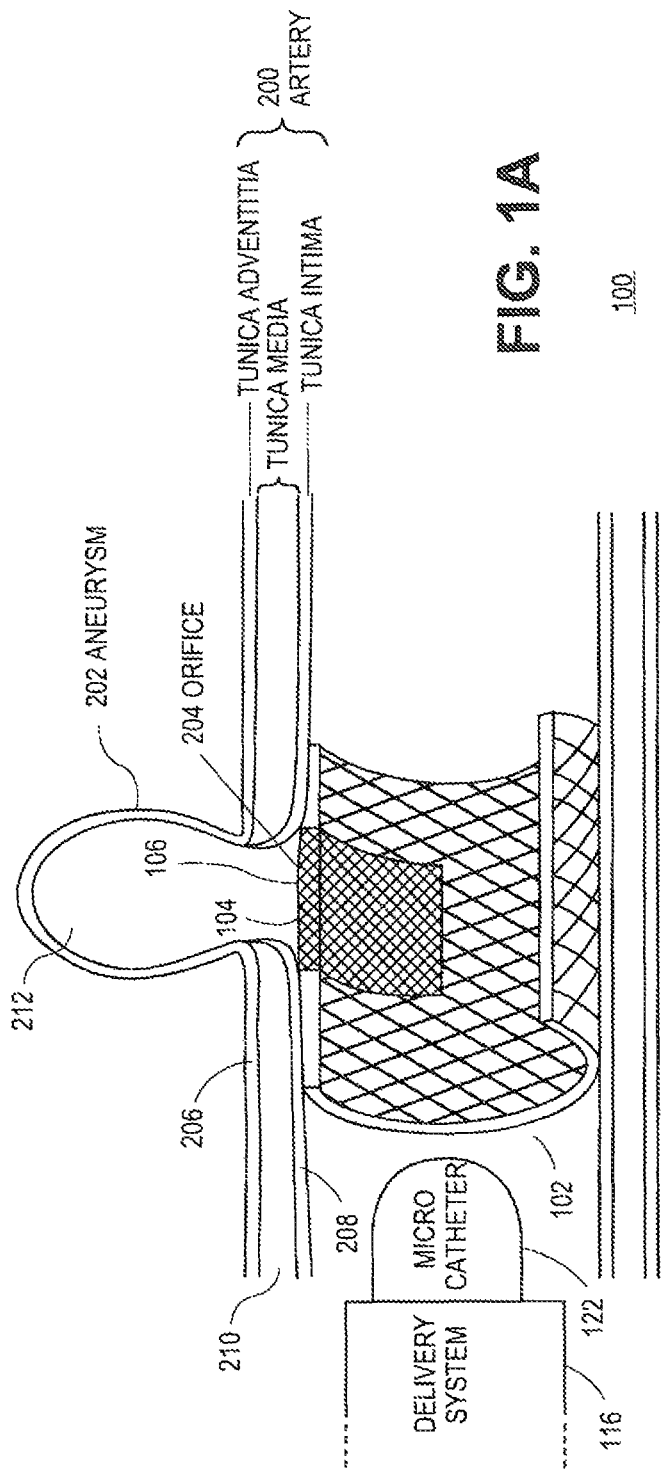
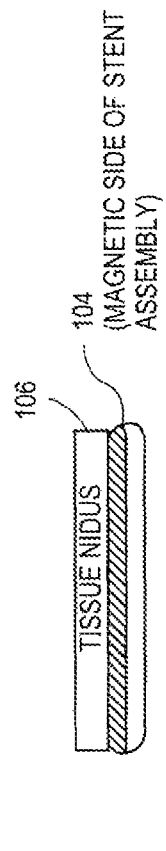
FIG. 1A
FIG. 1B

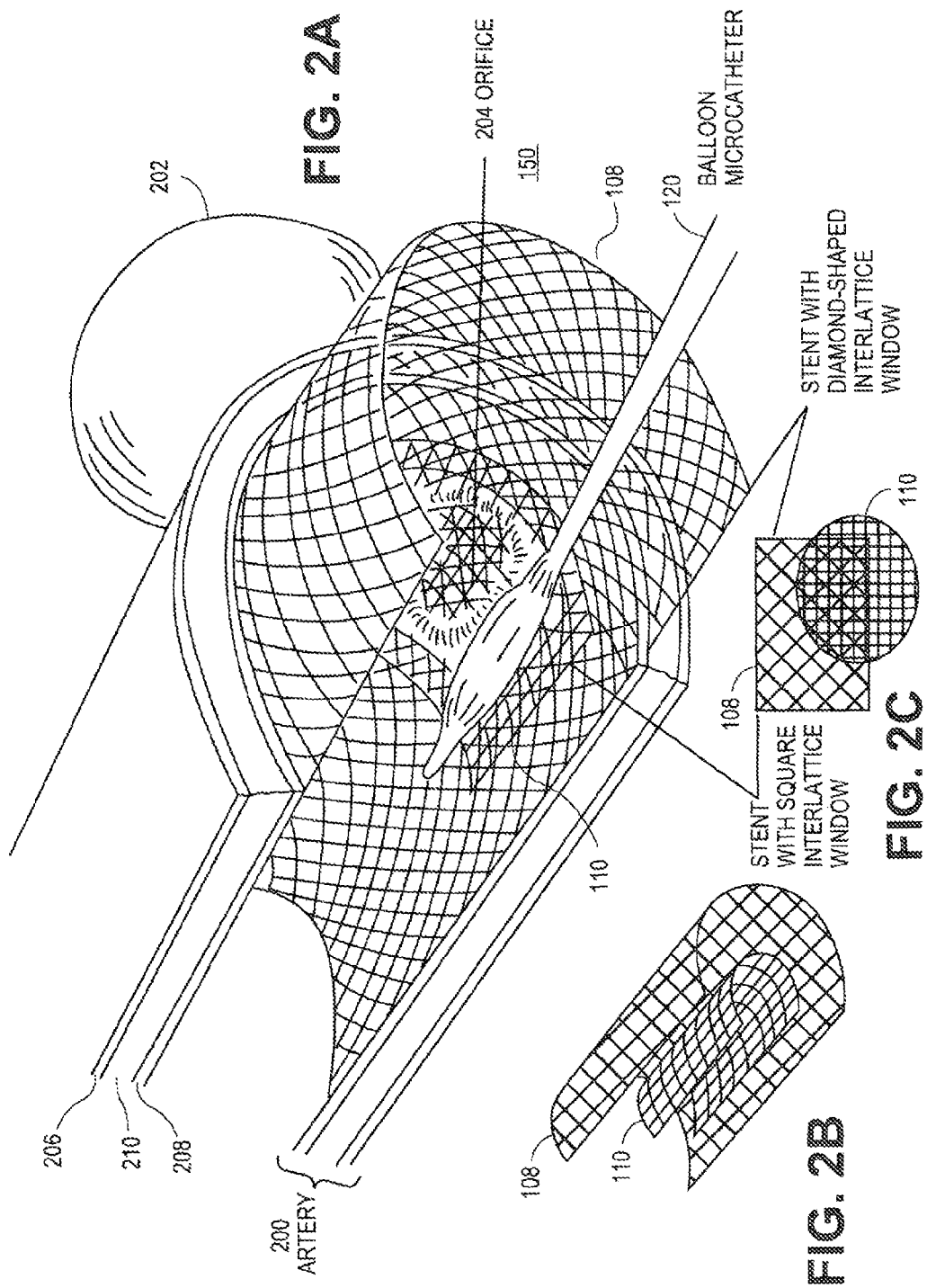

SYSTEMS AND METHODS FOR MAGNETIZED STENT HAVING GROWTH-PROMOTING PROPERTIES

REFERENCE TO RELATED APPLICATION

This patent application claims priority to U.S. Provisional Application Ser. No. 61/361,835, filed Jul. 6, 2010, which provisional application is incorporated in its entirety be reference herein.

GOVERNMENT INTEREST

This invention was made in part with Government support. The Government has certain rights in the invention.

FIELD

The present teachings relate to medical devices, and more particularly, to a magnetized stent having growth-promoting properties.

BACKGROUND OF RELATED ART

A vascular aneurysm is a localized bulge or bubble that forms in the wall of a weakened blood vessel. If left untreated, a vascular aneurysm continues to expand until it ruptures, causing a hemorrhage, resulting in other complications or death. Vascular aneurisms can be caused by any number of factors that lead to a weakened blood vessel wall, including hereditary factors, disease, or trauma. In the field of medical treatment of vascular aneurysms, various techniques have been attempted to protect the weakened vessel wall from further deterioration and possible rupture. Among those existing techniques include the application of an implanted clip or clamp, which provides a sealing force sufficient to keep the bubbled or distended area of the vessel closed. Another known technique is the use of endovascular coils of comparatively soft or springy wire-like material which are inserted through the orifice of the aneurysm, into the aneurysm sac itself.

Experience has shown that these techniques and others, unfortunately, suffer from certain drawbacks. In the case of aneurysm clipping, this approach necessitates an open craniotomy and the risks of wound infection, inadvertent injury to adjacent vascular structures and damage to the functionally eloquent nearby areas of the brain. In the use of an implanted coil which is performed using endovascular surgery, a minimally invasive approach, the coils themselves may be prone to unraveling and migration inside the parent artery of the aneurysm, which can require further surgery to re-position the coils or to perform other corrective actions. Although durability of treatment is provided by aneurysm clipping since the defect across the aneurysm neck or its orifice is drawn together by the clip re-establishing the weakened blood vessel wall, the attendant risks of open surgery for this procedure makes this the less favorable choice when compared to a minimally invasive procedure. In existing treatment using endovascular methods for coiling aneurysms, there is also minimal or no tissue re-growth across the orifice, which provides little or no relief in terms of fluid buildup or pressure inside the aneurysm itself. It may be desirable to provide systems and methods for a magnetized stent having growth-promoting properties, which, among other advantages, may allow sufficient structural support and induction of tissue growth to effectively re-seal the orifice of the aneurysm, relieving fluid flow and pressure in the aneurysm and significantly reducing or eliminating the possibility of a later rupture of the damaged vessel.

DESCRIPTION OF THE DRAWINGS

The accompanying drawings, which are incorporated in and constitute a part of this specification, illustrate embodiments of the present teachings and together with the description, serve to explain the principles of the present teachings. In the figures:

FIG. 1A illustrates an overall stent assembly for a magnetized stent having growth-promoting properties, according to various embodiments;

FIG. 1B illustrates a side view of a circumferential wall of a tubular elongated body, according to various embodiments;

FIG. 2A illustrates an overall stent assembly for a magnetized stent having growth-promoting properties, according to further various embodiments; and FIGS. 2B-2D illustrate various side or inclined views of the circumferential walls of tubular elements in a stent assembly, according to the further various embodiment shown in FIG. 2A.

SUMMARY

Figure 2D:
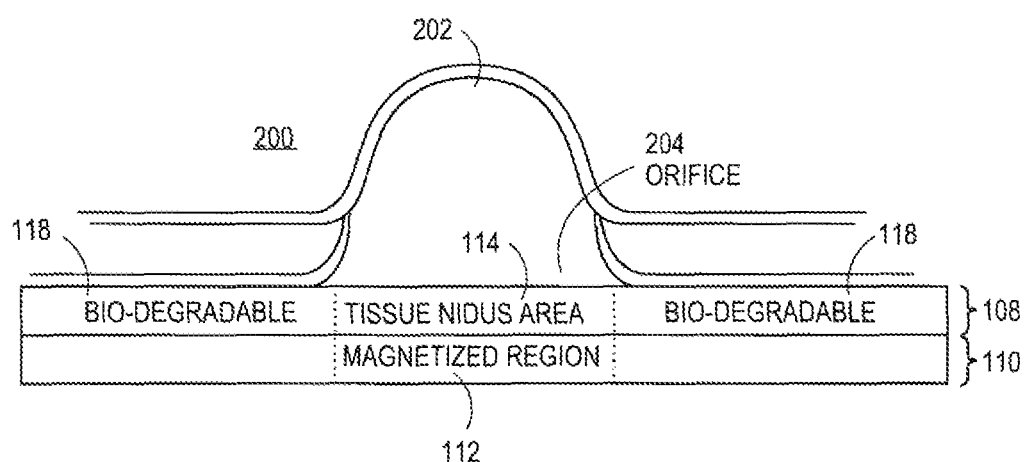

Embodiments of the present teachings relate to systems and methods for magnetized stent having growth-promoting properties. More particularly, embodiments relate to a novel stent assembly and associated techniques including the use of a stent structure having a magnetized region focused on or directed to the orifice of a vascular aneurysm or other blood vessel defect from one side of the stent circumference. The resulting local magnetic field can serve to attract cells comprising magnetic nanoparticles or magnetic or paramagnetic components of tissue or blood, such as methehemoglobin-bearing red blood cells or other elements of blood, to the area of the orifice. The area of the outer circumference of the stent assembly facing the orifice of the aneurysm can also have a tissue nidus area that can be treated or impregnated with a tissue growth medium and/or smooth muscle cells. While the tubular mesh body of the stent can provide a rigid structural support to maintain the integrity of the injured blood vessel, the local magnetized region can preferentially attract cells and other factors having magnetic properties, which when concentrated in the same area as the tissue nidus area, can promote or induce the growth of tissue, such as vessel lining or muscle layers (e.g. tunica intima, tunica media, or tunica adventitia), particularly across the aneurysm orifice or other blood vessel defect. According to aspects, the magnetized stent assembly having growth promotion properties and related techniques can thereby achieve partial or total sealing of vessel aneurysms, while requiring only a correct initial surgical placement and with little or no risk of required reparative procedures later.

These and other embodiments described herein address the various noted shortcomings in known stent technology, and provide a physician, patient, or others with an enhanced stent design providing surgical and clinical effectiveness in reinforcing and healing vascular aneurysms and/or other injuries or defects.

DETAILED DESCRIPTION

Reference will now be made in detail to exemplary embodiments of the present teachings, which are illustrated in the accompanying drawings. Where possible the same reference numbers will be used throughout the drawings to refer to the same or like parts.

FIG. 1A illustrates a stent assembly 100 according to aspects of the present teachings. In embodiments as shown, the stent assembly 100 can comprise a tubular elongated body 102. In aspects, the tubular elongated body 102 can be or include a patterned mesh or lattice, for example arranged in a sinusoidal, diamond, square, circular, or other pattern. In embodiments, the tubular elongated body 102 can be made of a compressible and/or expandable material or materials. In aspects, that material can be or include a metal or metals, such as stainless steel or nitinol. In aspects, nitinol may be preferred due to its resistance to deformation in a hemodynamic environment. In embodiments, that material can also or instead include non-metallic materials, such as plastic materials, biodegradable materials, or others. The tubular elongated body 102 can be fashioned to be of proportion and type to be inserted into a blood vessel or other lumen or tissue using a catheter delivery system, which, as understood by persons skilled in the art, can generally involve the mechanical transport and insertion of the stent assembly 100 using a narrow, hollow, conductive tube or microcatheter 122 operated by a surgeon or other clinician.

In aspects as shown, the tubular elongated body 102 can comprise or can have associated with it a magnetized region 104. In aspects, the magnetized region 104 can be or include a permanently magnetized area, region, and/or section of the tubular elongated body 102 intended to be generally positioned beneath, under, and/or otherwise in contact with, proximal, or adjacent to an aneurysm orifice or other area of the subject tissue to which treatment is to be directed. In aspects, toward that end, the magnetized region 104 can be provided in a region of the tubular elongated body 102 extending in a partial circumferential region of the tubular elongated body 102, intended to correspond to or overlap with the aneurysm orifice or other area of tissue targeted for treatment. In aspects, the magnetized region 104 can be impressed only in an outward-facing region of the tubular elongated body 102, so as to direct a magnetic field toward the aneurysm orifice or other area of tissue targeted for treatment, but not in the interior lumen of the tubular elongated body. In aspects, the partial circumferential region of the tubular elongated body 102 which can be permanently magnetized can include any desired radial cross-section of the tubular elongated body 102, such as, for example, one-half of the circumference of the tubular elongated body 102, or less. The permanent magnetization of the desired region of the tubular elongated body 102 can be impressed upon the tubular elongated body 102 by techniques known to persons skilled in the art, such as by using the application of electric and/or magnetic fields to the desired magnetized region 104. Magnetization of the magnetized region 104 can be produced by exposing or contacting the desired magnetized region 104 with existing magnetic materials, including but not limited to exposure to neodymium magnets. In these or other embodiments, to improve the magnetic properties of the magnetized region 104, the tubular elongated body 102 can be coated with a metal, including but not limited to nickel.

Magnetization of the magnetized region 104 can also or instead be produced by exposure of the magnetized region 104 to magnetized nanoparticles to confer magnetic polarization. In such aspects, nanoparticles can be synthesized on the surface of the tubular elongated body with heavy-ion beam irradiation. The conferring of a magnetic polarity in the magnetized region 104 can cause the outer surface of that region to have localized, magnetic properties, the ability to promote tissue growth, and improved biocompatibility. Magnetization of the magnetized region 104 can also or instead be produced using other materials or techniques.

In embodiments as shown in FIG. 1A, the tissue to which treatment is to be directed using the stent assembly 100 can be or include an artery 200, such as a human artery located in the heart, the brain, and/or other organs or body areas. The artery 200 can comprise layers of endothelial or muscle cells including a tunica media 210, a tunics intima 208, and a tunics adventitia 206. In aspects, the defect, injury, or condition to which treatment using the stent assembly 100 is to be conducted can be or include an aneurysm 202 including a cavity 212 (i.e., an aneurysm sac) and an orifice 204 formed in the artery 200, creating an outwardly bulging or extended bubble or deformation in the artery 200. It may be noted that in aspects, the aneurysm 202 can be formed or created by traumatic events such as blunt trauma, penetrating brain injury, explosive shock, strokes, and/or other causes, including those that can be produced in wartime environments, or as a result of other scenarios. In aspects, the typical size or diameter of the cavity 212 may be on the order of 3 mm, although larger and smaller sizes may also be presented. The typical size or diameter of the orifice 204 can be on the order of one-third of the size of the cavity 212, or approximately 1 mm, although larger or smaller diameters may be presented.

In aspects as likewise shown, the stent assembly 100 can also comprise a tissue nidus area 106. As used herein, the "tissue nidus area 106" refers to an area of the tubular elongated body 102 of the stent assembly 100 that promotes the growth of tissue, such as the tissue of a blood vessel, including, but not limited to, the tunica intima 208, tunica media 210. and/or tunica adventitia 206. Among the layers of the vessel wall of artery 200, it is the smooth muscle layer, or tunica media 210, that is missing in the area of aneurysm development. The smooth muscle layer or tunica media 210 provides the wall of blood vessel 200 with the resilience needed to maintain its integrity, despite variations in blood pressure buildup. Reconstruction of the tunica media 210 across the orifice 204 therefore promotes durability of treatment.

The tissue nidus area 106 can, if desired, be treated with growth-promoting medium, tissue, cells, and/or other material. In aspects, the tissue nidus area 106 can, for instance, include smooth muscle cells, including mammalian cells such as porcine coronary smooth muscle cells or histocompatible human smooth muscle cells. Porcine grafts have been used for human vascular grafts without showing signs of rejection. The growth-promoting material in the tissue nidus area 106 can likewise include material such as peroxisome proliferators activated receptor- gamma (PPAR-gamma), and/or other media or materials. In aspects, the growth-promoting medium, tissue, cells, and/or other material can be applied, adhered, injected, or attached in or to the tubular elongated body 102 as a paste, a wafer, and/or tissue fragments. In embodiments, the tissue nidus area 106 can comprise mammalian smooth muscle cells in which magnetic nanoparticles have been introduced and/or absorbed. In embodiments, the tissue nidus area 106 can be provided on an outer surface of the tubular elongated body 102, and/or can be interspersed in the mechanical cells or other interstitial areas between the skeletal mesh of the tubular elongated body 102.

As further illustrated in FIG. 1B, for example, the magnetized region 104 and tissue nidus area 106 can be arranged or configured to partially or totally overlap, with for instance the tissue nidus area 106 being oriented directly over and substantially or completely overlapping with the magnetized region 104. Other configurations or relationships between the position of the magnetized region 104 and tissue nidus area 106 can be used.

According to aspects, the stent assembly 100 can be inserted into a blood vessel or other tissue, and positioned to orient the magnetized region 104 and tissue nidus area 106 underneath the orifice 204. In aspects, the surgeon or other physician can introduce the stent assembly 100 into a blood vessel using a catheter-based or other delivery system 116, as understood by persons skilled in the art. The stent assembly 100 can be directed longitudinally through the blood vessel or other tissue to reach the area of the aneurysm 202, at which point the surgeon or other physician can rotate the stent assembly 100 to cause the magnetized region 104 and tissue nidus area 106 to be aligned or positioned underneath the orifice 204. In aspects, the stent assembly 100 can be secured into place in this position by releasing a microcatheter 122 located in the tip of the delivery system 116, allowing the stent assembly 100 to expand slightly into place due to the natural spring action of the mesh material of the tubular elongated body 102. In aspects, the positioning action can be aided by the use of endoscopic imaging systems, such as a camera located in the stent delivery system, by tomographic imaging devices, and/or by other imaging means. After insertion and positioning of the stent assembly 100 underneath the orifice 204 of the aneurysm 202, in aspects, smooth muscle cells laden with magnetic nanoparticles can be delivered via the microcatheter 122 or other channel or device within the aneurysm cavity 212, which encapsulated smooth muscle cells can react with the porous surface of the magnetized region 104 now covering the base of the aneurysm 202.

Upon proper orientation and placement of the stent assembly 100 underneath the orifice 204 of the aneurysm 202, the therapeutic action of the stent assembly 100 can thus be effected upon the aneurysm 202 through a combination of mechanical, magnetic, and/or bioactive effects to induce or promote the growth of healing tissue over the orifice 204 and other areas of the aneurysm 202. More particularly, in aspects, the presence of the magnetized region 104 can attract magnetic or paramagnetic constituents of blood or plasma in the area of the orifice 204, due to the short-range magnetic field established by the magnetized region 104. Residual blood left within the aneurysm cavity 212 are rendered paramagnetic due to disuse, and thus will adhere to the magnetized region 104 acting as a floor of the aneurysm orifice 204. The hemoglobin component in old circulating blood cells changes to methemoglobin as its ferrous ion changes to ferric, thus rendering residual red blood cells paramagnetic.

In embodiments, the presence of magnetic or paramagnetic constituents can be enhanced or promoted by the injection of magnetic nanoparticles into the cavity 212 through microcatheter 122 or other means, such as other channels of the delivery system 116, or others. In embodiments, the magnetic nanoparticles can become attached to or absorbed into blood cells, muscle cells, or other tissue or material, and thus be magnetically drawn to the area of the orifice 204. The attraction of magnetically treated or untreated hemoglobin molecules to the orifice 204 can, for example, promote the growth of vascular muscle or other tissue in the area of the orifice 204. In aspects, the outer surface of the tubular elongated body 102 can act as a mechanical support or structure upon which tissue growth can take place.

In addition to and combining with the growth-inducing properties of the magnetized region 104, the presence of the tissue nidus area 106 can further promote the growth of muscle and/or other tissue across the orifice 204. The tissue nidus area 106 can serve as a substrate for the establishment and growth of tissue across the orifice 204, providing cells, nutrients, and/or other growth factors to promote the development of replacement tissue across the orifice 204. In aspects, the presence of a growth-promoting medium in the interstitial spaces or other portions of the tubular elongated body 102 can likewise reduce the effective porosity of the stent assembly 100 across the boundary of the orifice 204, reducing fluid pressure in the aneurysm 202 and further helping to maintain the integrity of the affected vessel area against deterioration. In further embodiments, the various sections of the stent assembly 100 can be formed to have patterned meshes or lattices of different sizes, and thus, different porosities. For instance, the tissue nidus area 106 can be formed to have a smaller patterned mesh or lattice size than other sections of the stent assembly 100, and hence, have reduced porosity compared to regions of the tubular elongated body 102 located outside the tissue nidus area 106.

According to aspects, after implantation of the stent assembly 100 across the orifice 204, over time the combined structural, magnetic, and/or bioactive effects of the stent assembly 100 can cause replacement muscle and/or other tissue to grow across the complete diameter of the orifice 204 of the aneurysm 202. In one embodiment, the stent assembly promotes the growth of the tunics media 210 across the orifice 204. After sufficient time, the orifice 204 can become completely covered or sealed by that replacement tissue, cutting off any blood flow or leakage into the cavity 212 and significantly reducing or eliminating risks to the patient from the presence of the aneurysm 202.

FIG. 2A illustrates a magnetized stent assembly 150 having growth-promoting properties, according to further embodiments. In embodiments as shown, the stent assembly 150 can comprise a first tubular elongated body (or an outer tubular mesh 108), inside of which a second tubular elongated body (or an inner tubular mesh 110) is positioned or mounted. While inner tubular mesh 110 is illustrated as being of smaller size than outer tubular mesh 108 for ease of illustration, it should be noted that in embodiments, outer tubular mesh 108 can be smaller than inner tubular mesh 110, or in further embodiments the two meshes, outer tubular mesh 108 and inner tubular mesh 110, can be of the same size.

In aspects shown for instance in FIG. 2D, the outer tubular mesh 108 can comprise a tissue nidus area 114, which can be formed and configured in a similar manner to the same or similar tissue nidus areas described above in connection with embodiments illustrated in FIG. 1A. It may be noted that in embodiments, the outer tubular mesh 108 can be made of a biodegradable material 118, such as polyglycolic acid material or polylactic acid material, to permit the reabsorption of the outer tubular mesh 108 within the vessel area under treatment. In aspects, other materials, such as other materials used in biodegradable sutures or grafts, can also be used to form the outer tubular mesh.

In aspects, the inner tubular mesh 110 can comprise a stent assembly, such as a skeletal wire-mesh stent made of stainless steel, nitinol, or other material, as described above in connection with embodiments illustrated in FIG. 1A. In aspects for instance also shown in FIG. 2D, the inner tubular mesh 110 can in aspects be provided with a magnetized region 112, which can be formed and configured in a similar manner to the same or similar magnetized region described above in connection with FIG. 1A. In aspects, and as for instance shown in FIG. 2B, the inner tubular mesh 110 can comprise a tubular mesh structure which is inserted concentrically inside of the outer tubular mesh 108, for instance, after placement of outer tubular mesh 108 inside artery 200, during manufacture, during preparation before any surgical procedure, and/or at other times.

In aspects, and as for instance shown in FIG. 2C, the outer tubular mesh 108 and inner tubular mesh 110 can be made with different mesh or lattice patterns. In aspects, the two lattices of the outer tubular mesh 108 and inner tubular mesh 110 can be structurally designed to be at cross-lattices to, and/or to otherwise complement, one another. The two lattices can thereby in aspects grip or lock in place together. Those patterns can be or include a square repeating pattern or shape for the outer tubular mesh 108 and a diamond-shaped repeating pattern or shape for the inner tubular mesh 110, as shown. It will however be appreciated that additional or different patterns or shapes can be used for each of the outer tubular mesh 108 and inner tubular mesh 110.

According to aspects, the stent assembly 100 shown in FIG. 2A can be inserted in similar fashion to that described for embodiments noted in connection with FIG. 1A above, which is to say, generally involves placing the stent assembly 100 underneath the orifice 204. In aspects, the outer tubular mesh 108 can for instance be first inserted into artery 200 with magnetized region 112 positioned underneath orifice 204 using balloon catheter 120 or other device, followed by insertion of inner tubular mesh 110 inside of the outer tubular mesh 108 using the balloon catheter 120 or other device with magnetized region 112 positioned underneath and/or in partial or total alignment with the tissue nidus area 114, to form a stent-in-stent assembly. In aspects, the outer tubular mesh 108 and inner tubular mesh 110 can be inserted in other orders and/or configurations, for instance, by inserting inner tubular mesh 110 first followed by insertion of outer tubular mesh 108 second, inside or outside of the inner tubular mesh 110, to form other configurations or types of stent-in-stent assembly.

In aspects, positioning and locking outer tubular mesh 108 and inner tubular mesh 110 in place in such a manner can serve to situate or position the magnetized region 112 and tissue nidus area 114 in the orifice 204 and to direct the magnetic field, structural support, and/or bioactive effects of the stent assembly 100 to the orifice 204 of the aneurysm 202 formed in the subject vessel. It may be noted that in embodiments, the inner tubular mesh 110 can be formed without any special growth-medium, porosity, and/or other features. In aspects, the inner tubular mesh 110 can comprise a conventional and/or commercially available tubular body, which can be selectively magnetized in the magnetized region 112 and act as a support to outer tubular mesh 108. In embodiments, however, if desired, the inner tubular mesh 110 can also be formed with growth-medium or other features of its own, to augment the growth-promoting effects or benefits of the outer tubular mesh 108. It should be noted that in aspects, the surgical positioning of the stent assembly 150 shown in FIG. 2A does not require recourse to the use of a microcatheter 122 or other instrument inserted inside the aneurysm cavity 212 or sac to deliver magnetized cells or micelles.

It should be noted that while embodiments are described above in connection with the surgical treatment of an aneurysm 202 and associated features, the stent assembly 100 of the invention can be applied and/or adapted to other injuries, diseases, or defects. For instance, in the case of a heart containing a congenital defect such as a patent foramen ovale (PFO), the invention may be adapted to provide a one-faced magnetic disc on one side of the heart while providing a second (paramagnetic) disc on the other side of the heart, positioned around the defect opening. Other organs and/or conditions can be treated with magnetic, structural, and/or growth-promoting effects according to the present teachings.

The foregoing description is illustrative, and variations in configuration and implementation may occur to persons skilled in the art For example, while embodiments have been described in which the tubular elongated body 102 of the stent assembly 100 is illustrated as having a uniform diameter, in embodiments, the tubular elongated body 102 can be formed to have varying diameters along its length. For further example, while embodiments have been described in which the stent assembly 100 contains one magnetized region 104 and one tissue nidus area 106, in embodiments, the stent assembly 100 can be formed to contain more than one magnetized region 104 and/or more than one tissue nidus area 106. For yet further example, while stent-in-stent embodiments have been described in which one inner tubular mesh is nested within an outer tubular mesh, in embodiments, three or more tubular meshes or other structures can be nested in stent-in-stent fashion. For still further example, while embodiments have been described in which a stent assembly can be fashioned using a stent-in-stent configuration in which one stent can be made of metal material while the other stent can be made of biodegradable material, in embodiments, a stent assembly can be made in using a unitary configuration using a hybrid metal and biodegradable construction. Other elements or resources described as singular or integrated can in embodiments be plural or distributed, and elements or resources described as multiple or distributed can in embodiments be combined. The scope of the present teachings is accordingly intended to be limited only by the following claims.

What is claimed is:

1. A stent assembly, comprising:
a tubular elongated body having an inner and outer surface, wherein the tubular elongated body comprises:
a tissue nidus area comprising growth-promoting material positionable underneath an orifice of a vascular aneurysm, wherein the tissue nidus area is provided on the outer surface of the tubular elongated body and comprises an area of the tubular elongated body coated with muscle cells comprising magnetic nanoparticles; and
a magnetized region, alignable with the tissue nidus area, for applying a magnetic field to the orifice of the vascular aneurysm to promote tissue growth on the tissue nidus area and across the orifice.

2. The stent assembly of claim 1, wherein the tissue nidus area and the magnetized region are located on the outer surface of the tubular elongated body.

3. The stent assembly of claim 2, wherein the magnetized region comprises a magnetized region on the outer surface of the tubular elongated body extending over a portion of the circumference of the tubular elongated body.

4. The stent assembly of claim 3, wherein the portion of the circumference comprises at most one half of the circumference.

5. The stent assembly of claim 4, wherein the portion of the circumference comprises a circumscribed area corresponding to that of the orifice.

6. The stent assembly of claim 1, in which the tubular elongated body comprises an expandable tubular metal mesh.

7. The stent assembly of claim 6, wherein the tubular metal mesh comprises at least one of nitinol or stainless steel.

8. The stent assembly of claim 1, wherein the magnetized region comprises magnetized nanoparticles.

9. The stent assembly of claim 1, wherein the tissue nidus area is located on the outer surface of the tubular elongated body and the magnetized region is located on an inner tubular mesh concentrically mounted inside the tubular elongated body.

10. The stent assembly of claim 9, wherein the tubular elongated body is made of a biodegradable material.

11. The stent assembly of claim 1, wherein the tissue nidus area and the magnetized region at least partially overlap.

12. The stent assembly of claim 11, wherein the tissue nidus area and the magnetized region are coextensive.

13. The stent assembly of claim 1, wherein the muscle cells comprise mammalian vascular smooth muscle cells.

14. The stent assembly of claim 13, wherein the mammalian vascular smooth muscle cells comprise human or porcine vascular smooth muscle cells.

15. A method of treating a vascular aneurysm in a subject, comprising:
    introducing the stent assembly of claim 1 into a blood vessel of the subject, wherein the blood vessel comprises the vascular aneurysm; and
    positioning the tissue nidus area and the magnetized region underneath an orifice of the blood vessel to promote tissue growth across the orifice of the vascular aneurysm.

16. The method of claim 15, further comprising introducing cells comprising magnetized nanoparticles into the vascular aneurysm.

\* \* \* \* \*